(12) United States Patent
Orito et al.

(10) Patent No.: US 7,591,793 B2
(45) Date of Patent: Sep. 22, 2009

(54) INFANT MOVEMENT ANALYSIS SYSTEM AND INFANT MOVEMENT ANALYSIS METHOD

(75) Inventors: Kensuke Orito, Sagamihara (JP); Tomoaki Ikeda, Miyazaki (JP); Hiroshi Matsuda, Fuchu (JP)

(73) Assignee: Tokyo University of Agriculture and Technology (JP)

( * ) Notice: Subject to any disclaimer, the term of this patent is extended or adjusted under 35 U.S.C. 154(b) by 132 days.

(21) Appl. No.: 10/595,593

(22) PCT Filed: Oct. 15, 2004

(86) PCT No.: PCT/JP2004/015238

§ 371 (c)(1),
(2), (4) Date: Apr. 28, 2006

(87) PCT Pub. No.: WO2005/041770

PCT Pub. Date: May 12, 2005

(65) Prior Publication Data

US 2007/0016109 A1    Jan. 18, 2007

(30) Foreign Application Priority Data

Oct. 31, 2003    (JP)    ............... 2003-371506

(51) Int. Cl.
  *A61B 5/103*    (2006.01)
  *G06K 9/00*    (2006.01)
(52) U.S. Cl. .............. 600/595; 382/128; 128/923
(58) Field of Classification Search ........... 600/587, 600/595; 128/923; 382/128, 130
See application file for complete search history.

(56) References Cited

U.S. PATENT DOCUMENTS

2005/0004495 A1 * 1/2005 Goswami .................. 600/595

FOREIGN PATENT DOCUMENTS

| CA | 2458269 | 2/2004 |
| JP | 05-299122 | 5/1995 |
| JP | 7-124126 | 5/1995 |
| JP | 2003-371506 | 6/2003 |
| JP | 2003-210435 | 7/2003 |

OTHER PUBLICATIONS

Goswami, Ambarish. "A new gait parameterization technique by means of cyclogram moments: Application to human slope walking." Gait & Posture. 1998. vol. 8. pp. 15-36.*

(Continued)

*Primary Examiner*—Max Hindenburg
*Assistant Examiner*—John Pani
(74) *Attorney, Agent, or Firm*—Stephen Chin; von Simson & Chin

(57) ABSTRACT

A system which extracts motion data from a video image of an infant, and determines synchronism, symmetry, and/or coordination among the limbs. The system uses the synchronism, symmetry, and/or coordination results to determine whether the infant has a disease and/or what disease it may be. The system uses as an index for coordination one or more of: a movement start/stop order and acceleration of the markers; the trajectory, speed, or acceleration of a midpoint of a line connecting markers attached to various combinations of the arms and legs; and the trajectory, speed, and acceleration of a gravity center of a plane connecting three markers attached to various limbs.

5 Claims, 5 Drawing Sheets

OTHER PUBLICATIONS

Nicolas B. Karayiannis, et al. "Extraction of Motion Strength and Motor Activity Signals from Video Recordings of Neonatal Seizures"; IEEE Transactions on Medical Imaging, vol. 20, No. 9, Sep. 2001, p. 965-980.

Heinz F.R. Prechtl DM DPhil FRCOG (Hon); "General Movement Assessment as a Method of Developmental Neurology: New Paradigms and Their Consequences"; Developmental Medicine & Child Neurology 2001, 43: 836-842.

Page S105 of Abstracts / Gait and Posture 18(2003)S80-S123.

Program of Seminar held on Sep. 10-13, 2003.

PT Journal, No. 10, vol. 34, Oct. 2000—Evaluation On Body Movements Of Newborns And Premature Babies.

Collected Papers from BPES 2000I, 15th Biological And Physiological Engineering Symposium—3D Motion Analysis Of Spontaneous Movements Of Newborn And Young Infants.

* cited by examiner

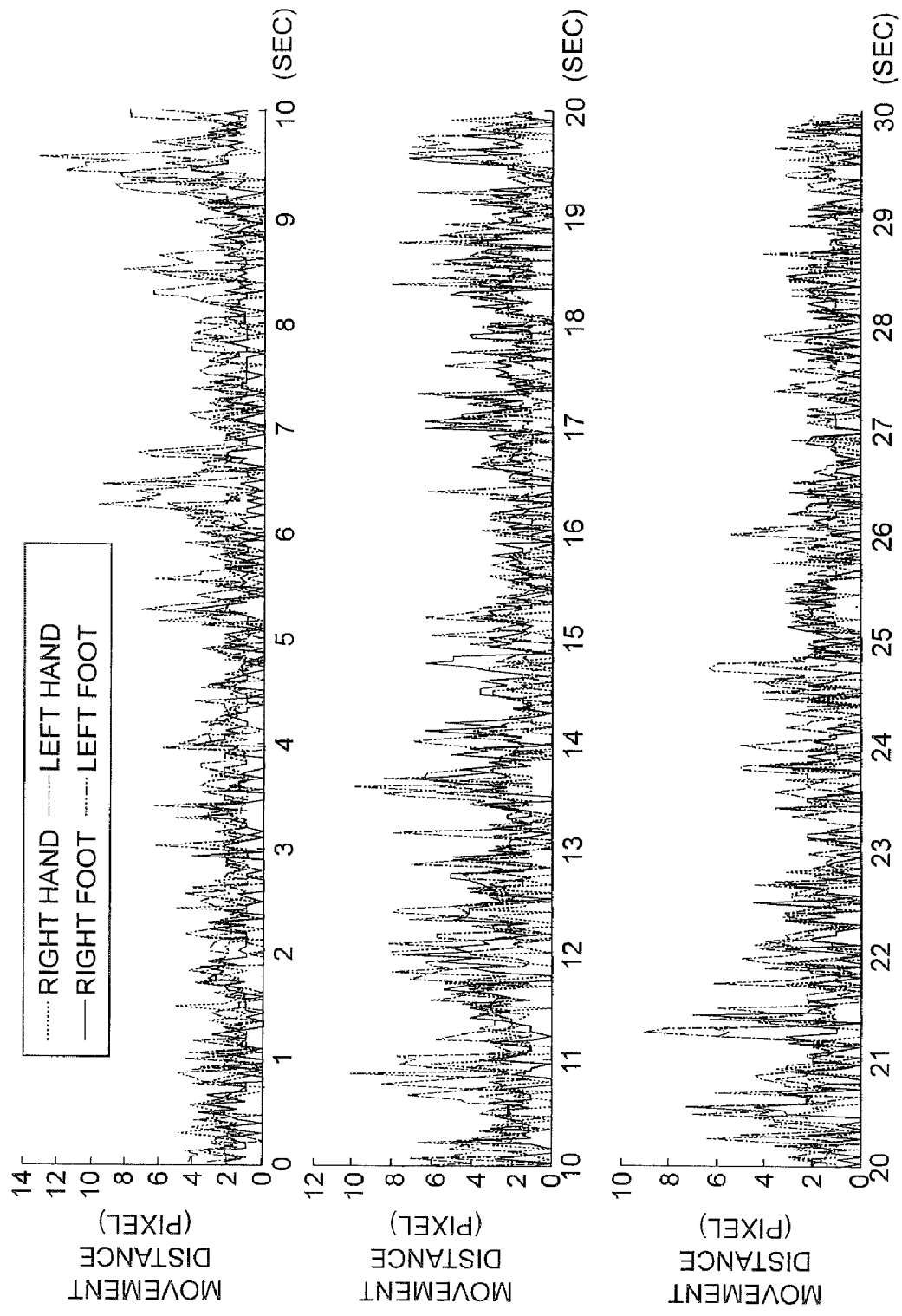

INFANT MOVEMENT ANALYSIS SYSTEM AND INFANT MOVEMENT ANALYSIS METHOD

CROSS-REFERENCES TO RELATED APPLICATIONS

This application is the United States National Phase of PCT Application No. PCT/JP2004/015238 filed on Oct. 15, 2004 and claims the benefit of Japanese Application No. 2003-371506 filed on Oct. 31, 2003, the entire contents of which are hereby incorporated by references herein.

TECHNICAL FIELD

The present invention relates to an infant movement analysis system and an infant movement analysis method for finding a disease and/or a symptom, or a sign thereof of an infant (including a newborn).

BACKGROUND ART

Unlike children and adults, infants (including newborns) are not capable of communication by means of words. Therefore, the state of an infant has to be conjectured only through observation.

Conventionally, a device for thus observing the state of an infant has been proposed (see, for example, Patent document 1: Japanese Translation of PCT Publication No. 2001-516253). In Patent document 1, a nose mask type pneumotachograph is used for a newborn to obtain its respiratory waveform, and various kinds of analyses are conducted based on the respiratory waveform.

Another possible method is to take an electrocardiogram from a newborn and conduct various kinds of analyses based on the electrocardiogram as is done for an adult. (see, for example, Patent document 1: claim 10, p. 17 "Summary of the Invention", and the third line from the bottom to the final line of p. 25).

DISCLOSURE OF THE INVENTION

Problems to Be Solved by the Invention

In the above-described methods, however, a nose mask and terminals for taking an electrocardiogram have to be attached to an infant (a newborn), and parents, when seeing their child wearing such instruments, suffer a heavy mental burden. Specifically, this kind of observation has to be conducted for all infants because it is not clear at the time of the observation whether or not the infants are normal, and parents seeing such a state unnecessarily feel concerned about the physical condition of their child. Further, attaching such instruments to an infant may possibly give a physical load to the infant.

Further, for example, an event in which a newborn is put under a hypoxic or anoxic condition at birth for some reason, if any, may possibly cause brain damage at a later time. However, even if the infant is observed with naked eyes, it is difficult to know that such an event occurred at birth. It is also difficult to know the possibility of the onset of such brain damage prior to the onset even by a diagnosis by a doctor, and it is not until an instant after the elapse of about half a year to about one year and a half from the birth that such brain damage is found. The brain damage of an infant (newborn) often becomes beyond cure, if treated after it is found, and early detection thereof at birth or in infancy is important. However, no approach to early detection for such a case has currently been established yet.

It is an object of the present invention to provide an infant movement analysis system and an infant movement analysis method which have a prospect to realize early detection of various kinds of diseases through the observation of an infant's state without attaching any measurement instrument to the infant and which can lighten a parent's mental burden ascribable to the observation.

Means to Solve the Problem

In order to solve the aforesaid problems, an infant movement analysis system of the present invention includes: an imaging device that photographs an infant to output a motion picture of the infant as digital data; and an analyzing device that determines movements of four limbs of the infant from the motion picture of the infant who is photographed by the imaging device and identifies a disease and/or a symptom of the infant from correlativity of movements of a plurality of arms and/or legs out of the four limbs.

With this, since a state of an infant is observed from the image obtained when the infant is photographed, it is not necessary to attach measurement instruments to the infant, which can lighten a parent's mental burden ascribable to the observation. Further, since the movements of the four limbs of the infant are observed and the movements of the four limbs peculiar to a disease are extracted, early detection of various kinds of diseases can be expected. These effects are prominent especially for a newborn whose disease existence is difficult to confirm.

Another infant movement analysis system of the present invention includes: a database that stores movement data indicating histories of movements of four limbs of an infant, the movements being determined from a motion picture of the infant photographed by an imaging device that photographs an infant to output a motion picture of the infant as digital data; and an analyzing device that identifies a disease of the infant from correlativity of movements of a plurality of arms and/or legs out of the four limbs, based on the movement data stored in the database.

With this, since a state of an infant is observed from an image obtained when the infant is photographed, it is not necessary to attach measurement instruments to the infant, which can lighten a parent's mental burden ascribable to the observation. Further, since the movements of the four limbs of the infant are observed and the movements of the four limbs peculiar to a disease (correlativity of the movements of arms (hands) and legs (feet)) are extracted, early detection of various kinds of diseases can be expected. These effects are prominent especially for a newborn whose disease existence is difficult to confirm.

Another infant movement analysis system of the present invention includes: a database that stores a plurality of movement data indicating histories of movements of four limbs of a plurality of infants, the movements being determined from motion pictures of the plural infants photographed by an imaging device that photographs an infant to output a motion picture of the infant as digital data; and an analyzing device that judges whether or not an infant newly photographed has a disease or not, according to a judgment condition which is set based on distribution of movement data of infants judged as normal infants with respect to the disease and/or distribution of movement data of infants judged as having the disease, out of the plural movement data stored in the database.

With this, since a state of an infant is observed from the image obtained when the infant is photographed, it is not necessary to attach measurement instruments to the infant, which can lighten a parent's mental burden ascribable to the observation. Further, since the movements of the four limbs peculiar to a disease are extracted based on the past data on normal infants or infants having the disease, early detection of various kinds of diseases can be expected. These effects are prominent especially for a newborn whose disease existence is difficult to confirm.

According to another infant movement analysis system of the present invention, in the infant movement analysis system of the above-described invention, the analyzing device is structured as follows. The analyzing device includes: a feature image extracting means for extracting, from the image of the infant, marker images of markers attached to the four limbs of the infant or feature images of the four limbs of the infant once every one frame or plural frames; a limb movement determining means for determining the movement of each of the limbs based on positions of the plural marker images or the plural feature images which are extracted in time series by the feature image extracting means; a movement analyzing means for extracting right-left synchronism of the arms or legs, right-left symmetry of the arms or the legs, and/or coordination among the plural limbs, in the movements of the four limbs determined by the limb movement determining means; and a judging means for judging existence/nonexistence or a value of possibility of a disease and/or a symptom of the infant based on degree of the right-left synchronism, the right-left symmetry, and/or the coordination which are extracted by the movement analyzing means.

With this, it is possible to quantify the movements of the four limbs of an infant which are difficult to visually quantify, so that the judgment can be made accurately and objectively based on the right-left synchronism, the right-left symmetry and/or the coordination.

According to another infant movement analysis system, in any one of the infant movement analysis systems of the above-described inventions, the feature image extracting means and the limb movement determining means are structured as follows. The feature image extracting means extracts a marker image of a reference point marker attached to at least one of head, breast, abdomen, and lumbar region other than the four limbs of the infant, and the limb movement determining means determines the movement of each of the limbs based on an absolute position of the marker image of each of the limbs in the image and/or a relative position of the marker image of each of the limbs to a position of the marker image of the reference point marker in the image.

With this, it is possible to extract the general movement of the body of the infant and the movement of each of the limbs separately, which enables more accurate determination of the movements of the four limbs of the infant.

According to another infant movement analysis system of the present invention, in any one of the infant movement analysis systems of the above-described inventions, the movement analyzing means is structured as follows. The movement analyzing means determines existence/nonexistence or the degree of the right-left synchronism, and/or the right-left symmetry of the arms or the legs, using as index at least one of: positions where the markers stop for a predetermined period or longer at a predetermined frequency or lower or at a predetermined frequency or higher; positions through which the markers pass at a predetermined frequency or lower or at a predetermined frequency or higher; movement ranges of the markers; space volumes by movements of the markers; kinetic momentums of the limbs determined based on the movements of the markers; and positions of the markers when the markers are at a specific speed, acceleration, and/or deceleration.

The use of at least one of the indexes enables accurate determination of the right-left synchronism and/or the right-left symmetry of the arms or the legs.

According to another infant movement analysis system of the present invention, in any one of the infant movement analysis systems of the above-described inventions, the movement analyzing means is structured as follows. The movement analyzing means determines existence/nonexistence or the degree of the coordination among the plural limbs, using as index one factor or a plurality of factors selected from: a movement start order and movement start accelerations of the markers when the markers start moving from a stop state; a movement stop order and movement stop decelerations of the markers when the markers stop from the moving state; at least one of a trajectory of a midpoint of a straight line connecting two markers attached to two right and left limbs out of the four limbs, speed of the midpoint, acceleration of the midpoint, and deceleration of the midpoint; at least one of a trajectory of a midpoint of a straight line connecting two markers attached to left arm and right arm, speed of the midpoint, acceleration of the midpoint, and deceleration of the midpoint; at least one of a trajectory of a midpoint of a straight line connecting two markers attached to left leg and right leg, speed of the midpoint, acceleration of the midpoint, and deceleration of the midpoint; at least one of a trajectory of a midpoint of a straight line connecting the two markers attached to the left arm and the right leg, speed of the midpoint, acceleration of the midpoint, and deceleration of the midpoint; at least one of a trajectory of a midpoint of a straight line connecting the two markers attached to the left leg and the right arm, speed of the midpoint, acceleration of the midpoint, and deceleration of the midpoint; and at least one of a trajectory of a gravity center of a plane or a solid including three or four markers attached to three limbs or four limbs out of the four limbs, speed of the gravity center, acceleration of the gravity center, and deceleration of the gravity center.

The use of at least one of these as an index enables accurate determination of the movement coordination among the plural limbs.

According to another infant movement analysis system of the present invention, in any one of the infant movement analysis systems of the above-described inventions, the markers attached to the four limbs of the infant are coated with or contain a substance that emits light when receiving ultraviolet, or a phosphor.

This enables the observation of an infant during night and in a dark place, so that daylong continuous observation is made possible.

An infant movement analysis method of the present invention includes the steps of: photographing an infant and converting a motion picture of the infant to digital data; determining movements of four limbs of the infant from the motion picture of the photographed infant; and identifying a disease and/or a symptom of the infant from correlativity of movements of a plurality of arms and/or legs out of the four limbs.

With this, since a state of the infant is observed from the image which is obtained when the infant is photographed, it is not necessary to attach measurement instruments to the infant, which can lighten a parent's mental burden ascribable to the observation. Further, the movements of the four limbs of the infant are observed and the movements of the four limbs peculiar to a disease are extracted, early detection of various kinds of diseases can be expected. These effects are prominent especially for a newborn whose disease existence is difficult to confirm.

Another infant movement analysis method of the present invention includes the steps of: by using a database that stores a plurality of movement data indicating histories of movements of four limbs of a plurality of infants, which are determined from motion pictures of the plural infants photographed by an imaging device that photographs an infant to output a motion picture of the infant as digital data, generating a judgment condition based on distribution of movement data of infants judged as normal with respect to a disease and/or distribution of movement data of infants judged as having the disease, out of the plural movement data stored in the database; and judging, according to the generated judgment condition, whether or not a newly photographed infant has the disease.

With this, since a state of an infant is observed from the image which is obtained when the infant is photographed, it is not necessary to attach measurement instruments to the infant, which can lighten a parent's mental burden ascribable to the observation. Further, since the movements of the four limbs peculiar to a disease is extracted based on past data on normal infants or infants having the disease, so that early detection of various kinds of diseases can be expected. These effects are prominent especially for a newborn whose disease existence is difficult to confirm.

An infant movement analysis system of the present invention includes: an imaging device that photographs an infant to output a motion picture of the infant as digital data; and an analyzing device that determines a movement of a marker attached to at least one limb out of four limbs of the infant, from the motion picture of the infant photographed by the imaging device and identifies a disease and/or a symptom of the infant from the determined movement of the marker.

With this, since a state of an infant is observed from the image which is obtained when the infant is photographed, it is not necessary to attach measurement instruments to the infant, which can lighten a parent's mental burden ascribable to the observation. Further, since the movement of the infant is observed and the movement of one limb or a plurality of limbs peculiar to a disease is extracted, so that early detection of various kinds of diseases can be expected. These effects are prominent especially for a newborn whose disease existence is difficult to confirm.

An infant movement analysis method of the present invention includes the steps of: photographing an infant and converting a motion picture of the infant to digital data; determining a movement of a marker attached to at least one of four limbs of the infant, from the motion picture of the photographed infant; and identifying a disease and/or a symptom of the infant from the determined movement of the marker.

With this, since a state of an infant is observed from the image which is obtained when the infant is photographed, it is not necessary to attach measurement instruments to the infant, which can lighten a parent's mental burden ascribable to the observation. Further, since the movement of the infant is observed and the movement of one limb or the plural limbs peculiar to a disease is extracted, early detection of various kinds of diseases can be expected. These effects are prominent especially for a newborn whose disease existence is difficult to confirm.

Effect of the Invention

According to the present invention, provided are an infant movement analysis system and an infant movement analysis method which are capable of observing a state of an infant without attaching any measurement instrument to the infant, and as a result capable of lightening a parent's mental burden ascribable to the observation.

BRIEF DESCRIPTION OF THE DRAWINGS

FIG. 5 is a chart showing an example of time-series movement data on four limbs.

EXPLANATION OF CODES

| | |
|---|---|
| 1 | analyzing device |
| 2 | imaging device |
| 4 | database |
| 12 | feature image extracting means |
| 13 | limb movement determining means |
| 14 | movement analyzing means |
| 15 | judging means |
| 201 | newborn (infant) |

BEST MODE FOR CARRYING OUT THE INVENTION

Hereinafter, embodiments of the present invention will be described based on the drawings.

Embodiment 1

Figure 1:
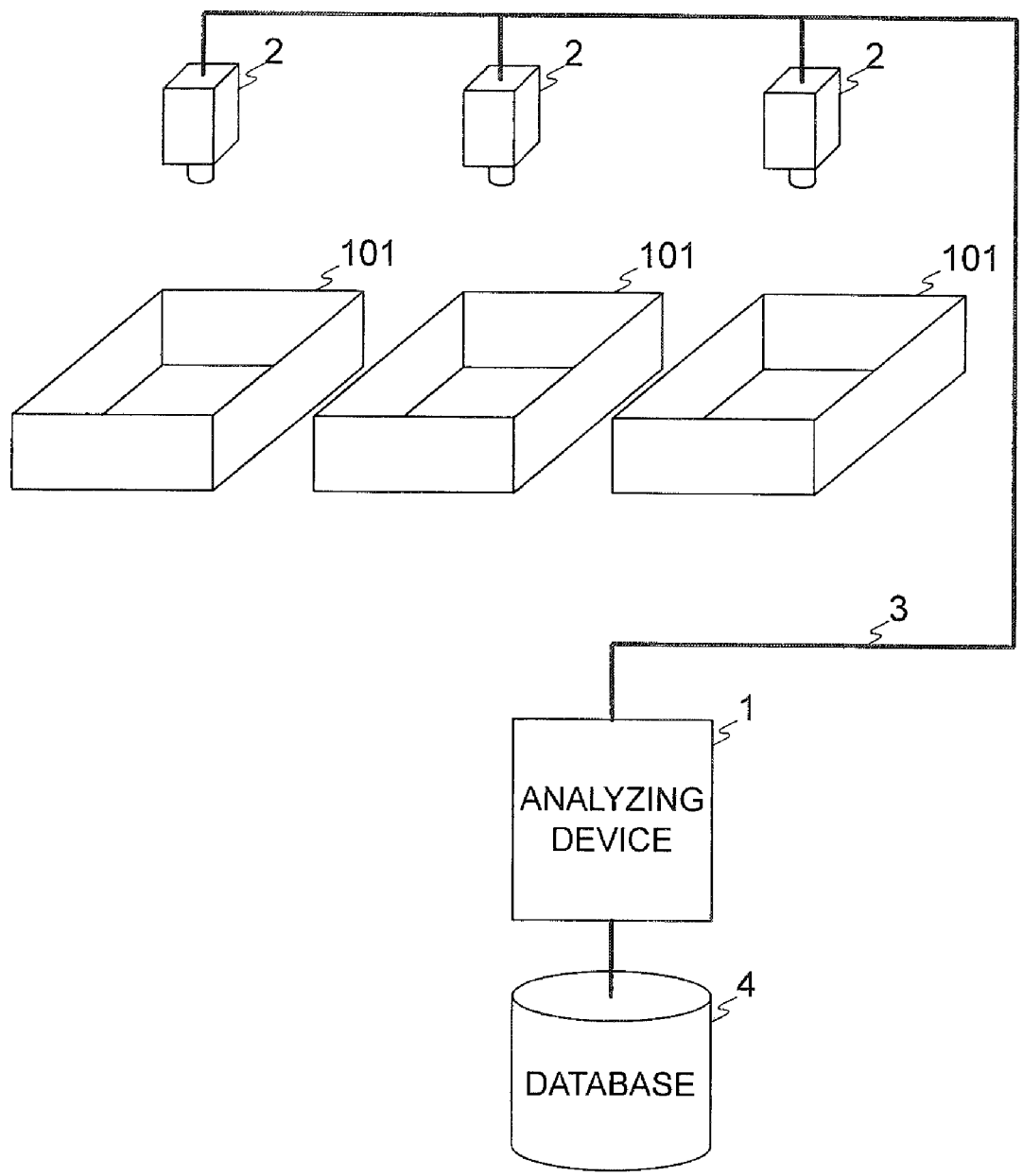
FIG. 1 is a view showing a configuration of an infant movement analysis system according to an embodiment 1 of the present invention.

FIG. 1 is a view showing a configuration of an infant movement analysis system according to an embodiment 1 of the present invention. In FIG. 1, an analyzing device 1 is a device that determines movements of four limbs of an infant from a motion picture of the infant photographed by an imaging device 2 and identifies a disease and/or a symptom of the infant from the correlativity of movements of a plurality of arms and/or legs out of the four limbs. This analyzing device 1 is realized by, for example, a computer having various kinds of interfaces and by programs.

The imaging device 2 is a device that photographs an infant to output a motion picture of the infant as digital data. As this imaging device 2, for example, a small-type CCD (Charge Coupled Device) camera is used. For photographing a newborn, the imaging device 2 is fixed on a newborn baby bed 101 or fixed on a ceiling of a newborn baby room. In FIG. 1, one imaging device 2 is disposed for one newborn baby bed 101, that is, for one newborn. However, one imaging device 2 may be disposed for the plural newborn baby beds 101.

A communication path 3 is a communication path for transmitting the digital data between the imaging devices 2 and the analyzing device 1. Examples used as the communication path 3 are various kinds of communication cables in conformity with data communication protocols.

Further, a database 4 is a recording medium storing movement data and so on. The movement data indicates histories of the movements of the four limbs of the infant which are determined from the motion picture of the infant photographed by the imaging device. As the database 4, for example, a large-scale recording device such as a hard disk drive is used. Note that the database 4 may be installed inside the analyzing device 1.

Figure 2:
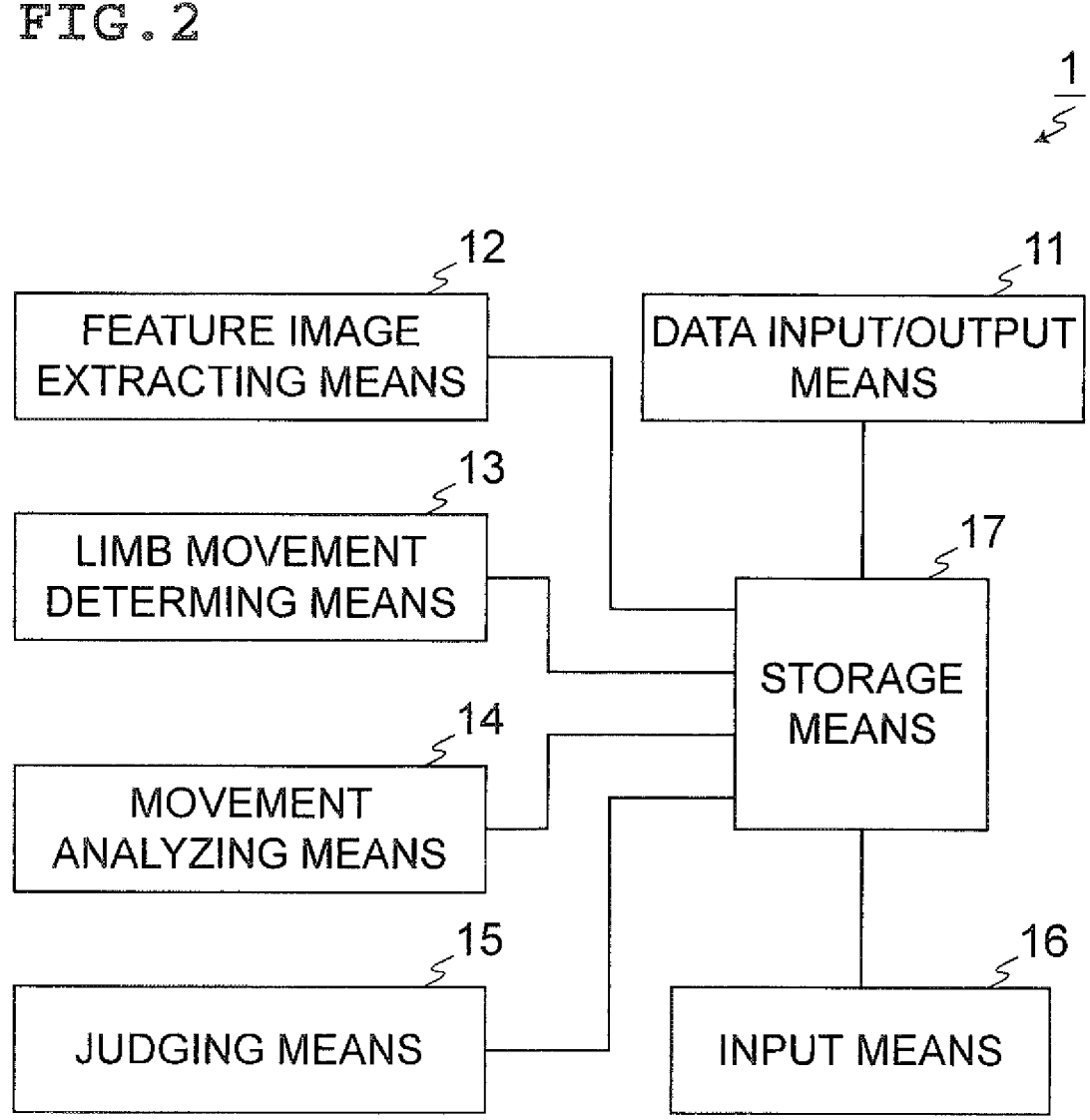
FIG. 2 is a block diagram showing a configuration of an analyzing device in the embodiment 1.

FIG. 2 is a block diagram showing a configuration of the analyzing device 1 in the embodiment 1. In FIG. 2, a data input/output means 11 is connected to the communication path 3 and the database 4 to receive the digital data from the imaging devices 2 and to transmit/receive various kinds of data to/from the database 4. A feature image extracting means 12 extracts, from the image of the infant, marker images of markers attached to the four limbs of the infant or feature images of the four limbs of the infant (for example, shapes, moles, birthmarks, and so on of the limbs) once every one frame or every plural frames.

A limb movement determining means 13 determines the movement of each of the limbs based on positions of the plural marker images or the plural feature images which are extracted in time series by the feature image extracting means 12. A movement analyzing means 14 extracts right-left synchronism of the arms or the legs, right-left symmetry of the arms or the legs, and/or coordination among the plural limbs, in the movements of the limbs determined by the limb movement determining means 13.

A judging means 15 judges the existence/nonexistence or possibility of a disease and/or a symptom of an infant based on the degree of at least one of the right-left synchronism, the right-left symmetry, and the coordination which are extracted by the movement analyzing means 14.

An input means 16 detects an operation by an operator such as a doctor to generate a signal according to the operation. A storage means 17 temporarily stores data transmitted/received by the data input/output means 11, processing results by the feature image extracting means 12, processing results by the limb movement determining means 13, processing results by the movement analyzing means 14, and so on.

Incidentally, when the analyzing device 1 is realized by a computer, part of the data input/output means 11 is realized by an interface circuit for peripheral equipment and/or a network interface circuit of the computer, the other part of the data input/output means 11, the feature image extracting means 12, the limb movement determining means 13, the movement analyzing means 14, and the judging means 15 are realized by a CPU of the computer executing predetermined programs, the storage means 17 is realized by a semiconductor memory of the computer, and the input means 16 is realized by a user interface such as a keyboard or a mouse connected to the computer. The programs executed by the CPU are stored in a ROM, a hard disk drive, or the like of the computer in advance.

Figure 3:
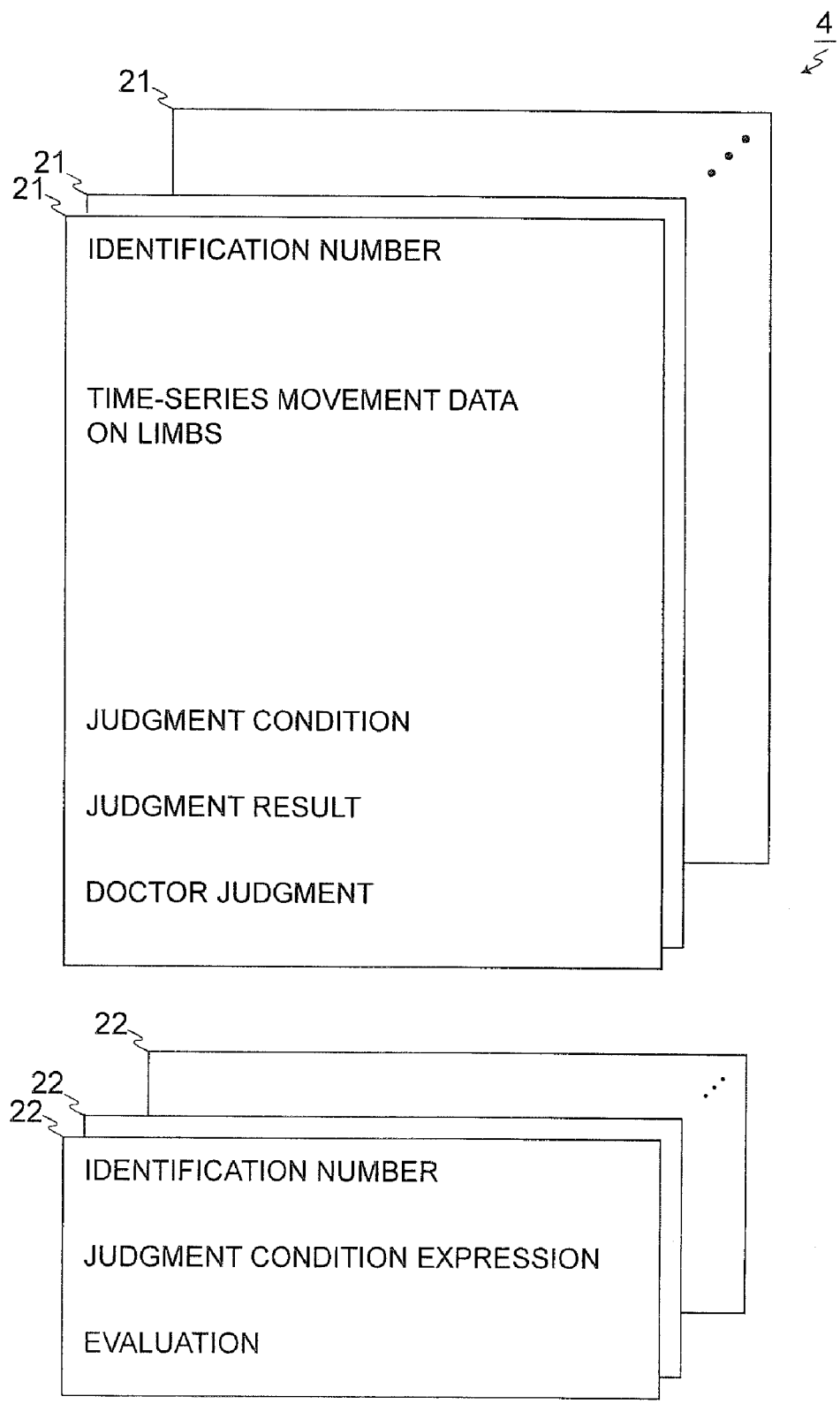
FIG. 3 is a view showing a structure of data stored in a database in the embodiment 1.

FIG. 3 is a view showing a structure of data stored in the database 4 in the embodiment 1. In FIG. 3, one newborn data 21 is generated for each newborn and it contains an identification number unique to the newborn baby bed 101, the imaging device 2, or a newborn, time-series movement data of the four limbs (hereinafter, referred to as movement data), judgment conditions used for judgment on the existence/nonexistence or the like of diseases (or identification numbers of the judgment conditions), judgment results under the judgment conditions, and diagnosis results of ex-post diagnosis of the newborn (hereinafter, referred to as doctor's judgment).

One judgment condition data 22 is generated for one judgment condition and it contains a unique identification number, a judgment condition expression, and evaluation for the judgment condition expression.

Next, the operation of the above-described system will be described.

First, markers are attached to a newborn. As the marker, used is paint applied on skin, a seal, a supporter, or the like. The marker is attached to fingertip of hand, palm, wrist, elbow joint, shoulder joint, toe tip, back of foot, ankle, knee joint, hip joint, and so on, and the plural markers are attached to a plurality of portions respectively.

Figure 4:
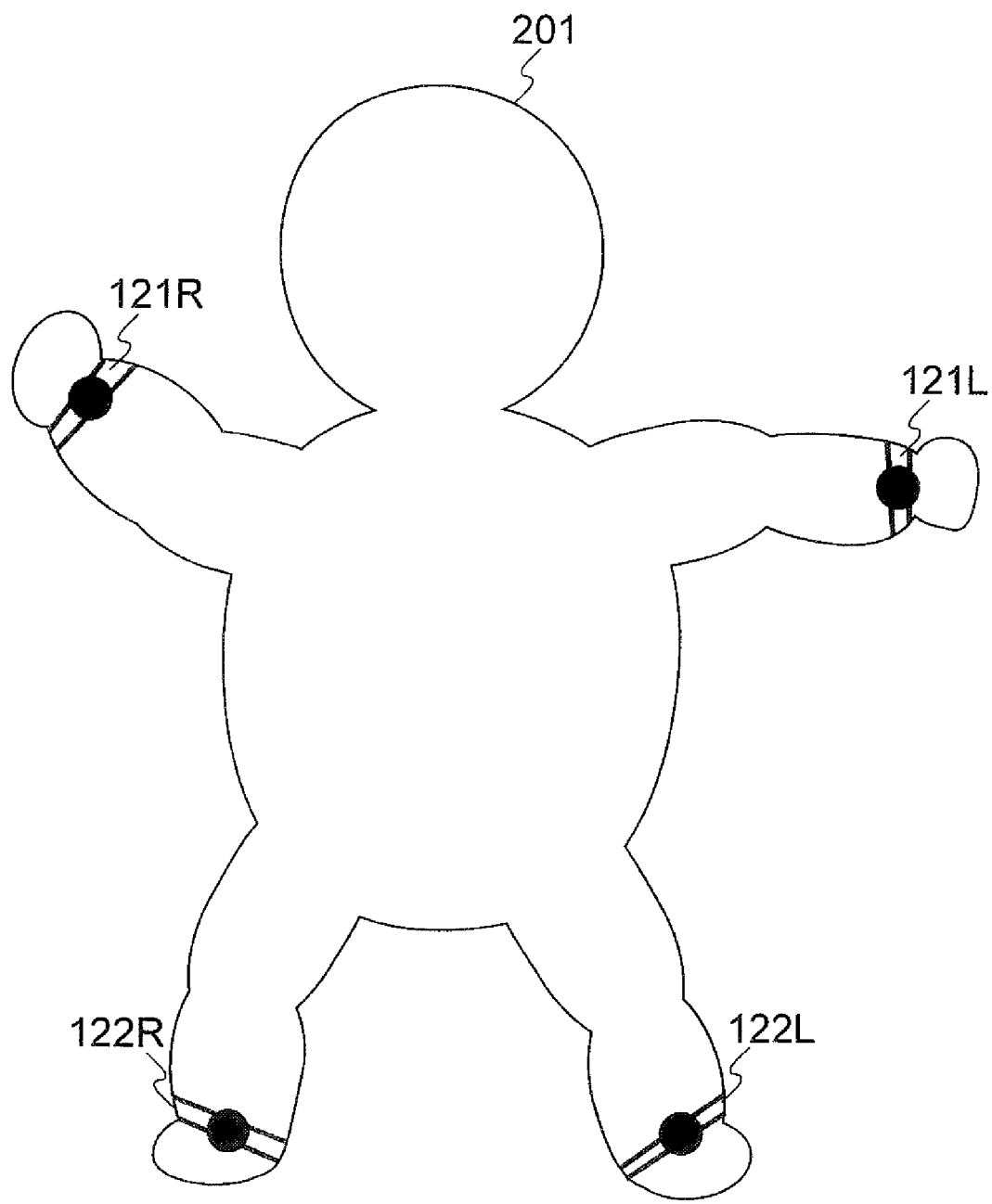
FIG. 4 is a view showing an example of a newborn to whom supporters each having a marker are attached.

FIG. 4 is a view showing an example of a newborn to whom supporters each having a marker are attached. In FIG. 4, a supporter 121R is attached to right wrist of a newborn 201, a supporter 121L is attached to left wrist of the newborn 201, a supporter 122R is attached to right ankle of the newborn 201, and a supporter 122L is attached to left ankle of the newborn 201. These supporters 121L, 121R, 122L, 122R have marks (black circles in FIG. 4) based on which positions of the supporters are extracted as feature images in a captured image.

After the markers are thus attached to the newborn 201, the imaging device 2 photographs the newborn to which the markers are attached, and supplies a motion picture of the newborn as digital data to the analyzing device 1 via the communication path 3.

The data input/output means 11 of the analyzing device 1 receives this motion picture data. This motion picture is composed of thirty frames (still images) per second and still image data of the respective frames in this motion picture data are stored in the storage means 17. Incidentally, in this embodiment, a frame rate is 30 frames per second but may be lower or higher. For example, a high-speed camera with a high frame rate may be used as the imaging device 2.

Next, the feature image extracting means 12 of the analyzing device 1 extracts the marker images of the markers attached to the four limbs of the infant or the features images of the four limbs of the infant from the still image data of the respective frames, determines the positions thereof in the frames, and stores data on the positions in the storage means 17. For example, when the markers shown in FIG. 4 are attached, areas with predetermined size and/or shape corresponding to the black circles shown in FIG. 4 are extracted from the still images.

Then, the limb movement determining means 13 of the analyzing device 1 determines the movement of each of the limbs based on position data on each of the markers which are extracted in time series and stored in the storage means 17 by the feature image extracting means 12. Specifically, the limb movement determining means 13 of the analyzing device 1 calculates the history of a physical kinetic momentum such as the position, speed, acceleration, or the like of each of the markers based on a series of the position data. The histories of these physical kinetic momentums determined by the limb movement determining means 13 are stored in the storage means 17 as movement data. Part or all of the movement data are stored in the database 4 as part of the newborn data 21 by the data input/output means 11. FIG. 5 is a chart showing an example of the time-series movement data on the four limbs. FIG. 5 shows, in a unit of pixel, a movement amount per frame in the image.

Incidentally, the movement of the marker which is a target of movement acquisition may be calculated based on an absolute value of the position of the marker in the captured image, or another possible method is to attach a reference point marker to at least one of head, breast, abdomen, and lumbar part in addition to the markers which are the targets of the movement acquisition and calculate the movement of each of the markers based on a position relative to a position of a marker image of the reference point marker. The reference point marker is made different from the markers as the targets of the movement acquisition in shape, size, pattern, color, or the like so as to be distinguishable from the markers as the targets of the movement acquisition. In this case, the feature image extracting means 12 of the analyzing device 1 extracts the marker image of the reference point marker, and the limb movement determining means 13 determines the movement of each of the limbs based on the position of the marker image of each of the limbs relative to the position of the marker image of the reference point marker.

When the movements of the markers are thus obtained, the movement analyzing means 14 of the analyzing device 1 extracts the right-left synchronism of the arms or the legs, the right-left symmetry of the arms or the legs, and/or the coordination among the plural limbs based on the movement data thereof. Specifically, a value of an index indicating the right-left synchronism of the arms or the legs, a value of an index indicating the right-left symmetry of the arms or the legs, a value of an index indicating the coordination among the plural limbs, and the like are calculated. The values of the indexes are stored in the storage means 17.

As the index indicating the right-left synchronism, at least one of the following is used:
(1) correlativity of movement speeds and accelerations (or decelerations) of the markers (correlativity in this case means the correlativity between right and left. The same applies to the following.),
(2) correlativity of movement speeds and accelerations (or decelerations) of the markers when arms or legs are stretched or bent,
(3) correlativity of movement vectors and its changes of the markers,
(4) correlativity of trajectories of the markers,
(5) correlativity of positions where the markers stop for a predetermined period or longer at a predetermined frequency or lower or at a predetermined frequency or higher,
(6) correlativity of positions through which the markers pass at a predetermined frequency or lower or at a predetermined frequency or higher,
(7) correlativity of movement ranges of the markers,
(8) correlativity of space volumes by the movements of the markers,
(9) correlativity of kinetic momentums of the limbs determined based on the movements of the markers, and
(10) correlativity of positions when the markers are at a specific speed, acceleration and/or deceleration. As the index indicating the right-left symmetry, at least one correlativity among the above is also used.

As the index indicating the coordination among the plural limbs, one factor or plural factors selected from the following is/are used:
(1) a movement start order and movement start accelerations of the markers at the start of the movement from a stop state,
(2) a movement stop order and movement stop decelerations of the markers at the time of stop from a moving state,
(3) at least one of a trajectory of a midpoint of a straight line connecting two markers attached to two right and left limbs out of the four limbs, speed of the midpoint, acceleration of the midpoint, and deceleration of the midpoint,
(4) at least one of a trajectory of a midpoint of a straight line connecting two markers attached to left arm and right arm, speed of the midpoint, acceleration of the midpoint, and deceleration of the midpoint,
(5) at least one of a trajectory of a midpoint of a straight line connecting left leg and right leg, speed of the midpoint, acceleration of the midpoint, and deceleration of the midpoint,
(6) at least one of a trajectory of a midpoint of a straight line connecting the two markers attached to the left arm and the right leg, speed of the midpoint, acceleration of the midpoint, and deceleration of the midpoint,
(7) at least one of a trajectory of a midpoint of a straight line connecting the two markers attached to the left leg and the right arm, speed of the midpoint, acceleration of the midpoint, and deceleration of the midpoint, and
(8) at least one of a trajectory of a gravity center of a plane or a solid including three or four markers of three limbs or four limbs out of the four limbs, speed of the gravity center, acceleration of the gravity center, and deceleration of the gravity center.

Incidentally, the positions, speeds, and accelerations of these midpoints and/or gravity center may be vectors.

The movements of the markers are thus analyzed, and one or plural index value(s) indicating the right-left synchronism, one or plural index value(s) indicating the right-left symmetry, and/or one or plural index value(s) indicating the coordination among the plural limbs are stored in the storage means 17. Then, the judging means 15 of the analyzing device 1 determines the existence/nonexistence or a value of possibility of a disease and/or a symptom of the infant, based on the value of the index indicating the degree of at least one of the right-left synchronism, right-left symmetry, and coordination which are extracted by the movement analyzing means 14.

At this time, the judging means 15 obtains the judgment condition data 22 regarding a predetermined disease from the database 4 via the data input/output means 11, applies the judgment condition to the value of the index of the right-left synchronism, the right-left symmetry and/or the coordination to determine the existence/nonexistence or the value of possibility of the disease and/or the symptom. For the judgment on the existence/nonexistence of the disease and/or the symptom, for example, the value of the index and a threshold value are compared. Further, for the judgment on the value of the possibility of the disease and/or the symptom, for example, the value of the possibility is calculated using a predetermined function with the value of the index being a variable.

This judgment condition is set as a range of the aforesaid value of the index based on the distribution of past movement data of infants judged as normal with respect to the relevant disease and/or the distribution of past movement data of infants judged as having the disease. That is, if the value of the index currently obtained from the newborn falls within the range of the value of the index which is set based on the distribution of the movement data of the infants judged as normal, it is judged that there is no existence (or low possibility) of the disease and/or the symptom, while otherwise, it is judged that there is the existence (or high possibility) of the disease and/or the symptom.

The judgment result by this judging means 15 is stored in the storage means 17, and the identification number of the judgment condition and the corresponding judging result are recorded as part of the newborn data 21 in the database 4 by the data input/output means 11. Incidentally, a display may be provided in the analyzing device 1 to display the judgment result, the newborn data 21, the judgment condition data 22, the history of the movement data, and so on.

Further, on a later day (several years later in some cases), a doctor examines this newborn (child) to judge whether or not the newborn (child) has an onset of a certain disease, and the doctor or another operator operates the input means 16 to input the diagnostic result (the aforesaid judgment by the doctor). The input means 16 of the analyzing device 1 stores data on the inputted doctor judgment in the storage means 17. Then, the data on the doctor judgment is recorded as part of the newborn data 21 for this newborn in the database 4.

Incidentally, another possible way is that the movement data, the judgment condition, the judgment result, and the doctor judgment are combined as one data set for each disease, and these data sets for a plurality of diseases regarding a certain newborn are recorded in the database 4 as part of the newborn data 21.

As in the foregoing, according to the embodiment 1 described above, the imaging device 2 photographs an infant to output a motion picture of the infant as digital data, and the analyzing device 1 determines the movements of the four limbs of the infant from the motion picture of the infant photographed by the imaging device 2 to identify a disease and/or a symptom of the infant from the correlativity of the movements of the plural arms and/or legs out of the four limbs.

Therefore, early detection of various diseases can be expected through the observation of the state of an infant. Further, it is possible to observe the state of an infant without attaching measurement instruments to the infant, so that a parent's mental burden ascribable to the observation can be lightened. Specifically, when conventional measurement instruments are used, cables extend from the measurement instruments, which arouses a concern of those seeing the infant that the infant may have some disease even if the infant is normal, but according to the system and method of the embodiment 1, only the markers need to be attached to an infant, and no cables need to be installed, which enables the observation of the state of an infant, in particular, a newborn without increasing a parent's concern.

Consequently, it becomes possible to know the possibility of a disease for a newborn before the onset of the disease, and therefore, by giving some treatment before its onset, the possibility of the onset can be expected to be lowered. For example, if a newborn is put under a hypoxic or anoxic condition at birth for some reason, early detection of a sign of brain damage can be expected.

Embodiment 2

In an infant movement analysis system according to an embodiment 2 of the present invention, movement data indicating histories of movements of four limbs of an infant which are determined from a motion picture of the infant photographed by an imaging device 2 are stored in a database 4, and thereafter, an analyzing device 1 reads the movement data stored in the database 4 to identify a disease of the infant from the correlativity of the movements of plural arms and/or legs out of the four limbs, based on the movement data, in a similar manner to that in the embodiment 1.

The configuration of the infant movement analysis system according to the embodiment 2 is the same as that of the embodiment 1, and therefore, description thereof will be omitted. However, in the embodiment 2, after movement data are calculated by a feature image extracting means 12 and a limb movement determining means 13 of the analyzing device 1 based on image data obtained from the imaging device 2, the movement data are recorded in the database 4. Thereafter, a movement analyzing means 14 of the analyzing device 1 reads the movement data from the database 4 to analyze them.

Embodiment 3

In an infant movement analysis system according to an embodiment 3 of the present invention, a judgment condition is created or updated by an analyzing device 1 based on the distribution of movement data of infants judged as normal with respect to a certain disease and/or the distribution of movement data of infants judged as having the disease, out of a plurality of movement data stored in a database 4.

Specifically, the analyzing device 1 reads to a storage means 17 the movement data which are judged as normal with respect to a certain disease (as not suggesting the disease) by doctor judgment, out of newborn data 21 in a database 4, and a movement analyzing means 14 calculates the aforesaid value of the index based on these movement data to determine a range of the value of the index of normal infants. This range is set based on the maximum value and the minimum value of the indexes obtained from the plural movement data.

Alternatively, the analyzing device 1 reads to the storage means 17 the movement data, with respect to a certain disease, which are judged as suggesting the disease by the doctor judgment, out of the newborn data 21 in the database 4, and the movement analyzing means 14 calculates the aforesaid value of the index based on these movement data, and determines the range of the value of the index of the infants having the disease. This range is set based on the maximum value and the minimum value of the indexes obtained from the plural movement data.

Alternatively, the range of the aforesaid value of the index of normal infants and the range of the value of the index of infants having the disease are both determined.

Thereafter, a judging means 15 of the analyzing device 1 makes the judgment, using the judgment condition which is created or updated based on the range of the value of the index thus obtained. For example, when the value of the index of an infant as a judgment target does not fall within the range of the value of the index of the normal infants, the judging means 15 judges that the infant has the disease (or the possibility of the disease exists).

The other configuration and operation of the infant movement analysis system according to the embodiment 3 are the same as those of the embodiment 1 or 2, and therefore, description thereof will be omitted.

As in the foregoing, according to the embodiment 3 described above, it is possible to observe the state of an infant and convert the state to data without attaching measurement instruments to the infant, so that a parent's mental burden ascribable to the observation can be lightened. Moreover, with the use of a large number of past data on infants, it is possible to create/correct the judgment condition regarding the existence/nonexistence of a disease, so that the judgment condition can be made accurate. As a result, as for a newborn, it becomes possible to know the possibility of the disease before its onset, so that by giving some treatment before the onset, the possibility of the onset can be expected to be lowered.

Embodiment 4

In an infant movement analysis system according to an embodiment 4 of the present invention, the analyzing device 1 of the embodiment 1 includes a warning means for nurse call or the like and when a judging means 15 judges that there exists an onset of a disease or a symptom (convulsion, seizure, or the like), the warning means notifies this by means of alarm or a communication device such as telephone.

The other configuration and operation of the infant movement analysis system according to the embodiment 4 are the same as those of the embodiment 1, and therefore description thereof will be omitted.

As in the foregoing, according to the embodiment 4 described above, this system can be used as a monitoring system for newborns, and if abnormality occurs, this is notified. As a result, it is possible to lighten workload such as monitoring of newborns by nurses. Further, in the embodiment 4, real-time detection of abnormality is possible, so that it also has a prospect to be utilized for preventing sudden infant death syndrome and for investigating an underlying cause thereof.

Embodiment 5

An infant movement analysis system according to an embodiment 5 of the present invention is structured such that in the embodiment 2, the analyzing devices 1 and the imaging devices 2 are installed in a plurality of hospitals, the analyzing device 1 and the database 4 are installed in a data collection center, and the analyzing devices 1 in the plural hospitals and the analyzing device 1 in the data collection center are made connectable by an electric communication line.

In the embodiment 5, after calculating movement data, each of the analyzing devices 1 in the plural hospitals transmits the movement data to the analyzing device 1 in the predetermined data collection center via the electric communication line. The analyzing device 1 in the data collection center records the movement data in a database 4 to analyze the movement data. Further, when doctor judgment is inputted to the analyzing device 1 of each of the hospitals at a later time, data on the doctor judgment are also transferred to the analyzing device 1 in the data collection center to be recorded together in the database 4. Note that in the embodiment 5, the same judgment condition data 22 may be stored in the analyzing devices 1 in the plural hospitals in advance for use, or the judgment condition data 22 stored in the database 4 in the data collection center may be obtained by the analyzing device 1 in each of the plural hospitals via the electric communication line.

The other configuration and operation of the infant movement analysis system according to the embodiment 5 are the same as those of the embodiment 2, and therefore description thereof will be omitted. Note that the function of creating/correcting the judgment condition in the embodiment 3 may be added to the infant movement analysis system according to the embodiment 5.

As in the foregoing, according to the embodiment 5 described above, it is possible to obtain the movement data on a large number of newborns from a plurality of hospitals. This as a result enables the use of a large number of data for creating/correcting the judgment condition, which makes it possible to obtain more accurate judgment condition in a short period.

It should be noted that the embodiments described above are preferred examples of the present invention, but the present invention is not limited to these embodiments and can be modified and changed in various ways without departing from the spirit of the present invention.

For example, in each of the embodiments, the markers attached to the four limbs of the infant may be coated with or contain a substance emitting light when receiving ultraviolet, or a phosphor. When the substance emitting light when it receives ultraviolet is used, a radiating device emitting feeble ultraviolet such as black light is provided together with the imaging device 2. This makes it possible to discriminate the markers in a captured image even during night, enabling continuous data collection and monitoring also during night.

Further, the above embodiments have described mainly the case of newborns, but the present invention is similarly applicable to infants from several months to about one year of age. In this case, the imaging device 2 is installed in a hospital room, home, or the like and image data is obtained by the analyzing device 1 in the hospital or the like.

Further, in the above-describe embodiments, the frames are all used, but the positions of the markers may be extracted only once every predetermined number of frames.

In the above-described embodiments, in recording and analyzing the movement data, the movement data may be classified into those obtained in a rest state, an excited state, a hungry state, and a sleeping state. In this case, the input means 16 of the analyzing device 1 may be operated so as to designate the rest state, the excited state, the hungry state, and the sleeping state. Then, in response to the operation, the analyzing device 1 classifies the movement data according to the designated classification to record the classified movement data in the database 4 as part of the newborn data 21.

Further, in the above-described embodiments, whether a symptom of an infant is getting better or worse may be recorded quantitatively as the transition of the value of the index by conducting longitudinal observation of the symptom that an infant has. This enables quantitative recording of spontaneous cure and medicinal effect, which can help the treatment.

In the above-described embodiments, the movements of the four limbs are determined based on the marker images and various kinds of judgments are made based on the movements of the four limbs, but the movements of one or plural number equal to four or less of the marker image(s) or one or plural number equal to four or less of limb(s) may be determined from the marker images and various kinds of judgments may be made based on this information. For example, the movement analysis may be made based on the movement of each of the markers. In this case, as the index, at least one of the following is used for one marker:

(1) movement speed and acceleration (or deceleration) of the marker,
(2) movement speed and acceleration (or deceleration) of the marker when arm or leg is stretched or bent,
(3) movement vector and vector change of the marker,
(4) trajectory of the marker,
(5) position where the marker stops for a predetermined period or more at a predetermined frequency or lower or at a predetermined frequency or higher,
(6) position through which the marker passes at a predetermined frequency or lower or at a predetermined frequency or higher,
(7) movement range of the marker,
(8) space volume by the movement of the marker,
(9) kinetic momentum of each limb determined based on the movement of the marker, and
(10) position of the marker when the marker is at a specific speed, acceleration and/or deceleration. Then, the existence/nonexistence and/or possibility or the like of a disease are/is judged based on whether or not the value(s) of one index or the plural indexes satisfies (satisfy) the judgment condition that is extracted from past similar data on normal infants or infants having the disease.

In the above-described embodiments, an image of a newborn may be analyzed/judged in real time immediately after (or within a predetermined time after) the newborn is photographed (that is, real-time analysis may be performed). This makes it possible to detect a disease or a symptom at an early stage, enabling early start of treatment.

In the embodiment 5 described above, the movement data are transmitted from the analyzing devices 1 in the respective hospitals to the analyzing device 1 in the data collection center, but another possible method is to transmit motion picture data from the imaging devices 2 in the respective hospitals to the imaging device 1 in the data collection center and extract the movement data from the motion picture data by the analyzing device 1 in the data collection center.

Further, in the above-described embodiments, another adoptable structure is to store the motion picture data as it is, instead of the movement data, in the database 4 and extract the movement data from the motion picture data by the analyzing device 1 at the time of the analysis.

INDUSTRIAL APPLICABILITY

The present invention is applicable to, for example, early detection of a disease of an infant. In addition, the present invention is applicable to, for example, a nurse call system. Further, the present invention is applicable to, for example, keeping track of disease status.

The invention claimed is:

1. An infant movement analysis system comprising:
   an imaging device that is configured to photograph an infant to output a motion picture of the infant as digital data; and
   an analyzing device that is configured to determine movements of four limbs of the infant from the motion picture of the infant who is photographed by said imaging device and identifying a disease and/or a symptom of the infant from correlativity of movements of a plurality of arms and/or legs out of the four limbs
   wherein said analyzing device includes: a feature image extracting means for extracting once every one frame or plural frames, from an image of the infant, marker images of markers attached to the four limbs of the infant or feature images of the four limbs of the infant;
   a limb movement determining means for determining the movement of each of the limbs based on positions of the marker images or the feature images which are extracted in time series by said feature image extracting means;
   a movement analyzing means for extracting from the movements of the four limbs determined by said limb movement determining means at least one of right-left synchronism of the arms or the legs, right-left symmetry of the arms or the legs, and coordination among the limbs; and
   a judging means for judging at least one of existence/nonexistence of a disease, a value of possibility of a disease and a symptom of the infant based on at least one of degree of the right-left synchronism, the right-left symmetry, and the coordination, which are extracted by said movement analyzing means
   wherein said movement analyzing means is configured to determine existence/nonexistence of the coordination among the limbs, or a degree of the coordination among the plural limbs, using as index one factor or a plurality of factors selected from:
   a movement start order and movement start accelerations of the markers when the markers start moving from a stop state;
   a movement stop order and movement stop decelerations of the markers when the markers stop from the moving state;
   at least one of a trajectory of a first midpoint of a straight line connecting a marker attached to a right arm and a marker attached to a right leg, speed of the first midpoint, acceleration of the first midpoint, and deceleration of the first midpoint;
   at least one of a trajectory of a second midpoint of a straight line connecting a marker attached to a left arm and a marker attached to a left leg, speed of the second midpoint, acceleration of the second midpoint, and deceleration of the second midpoint;
   at least one of a trajectory of a third midpoint of a straight line connecting a markers attached to a left arm and a marker attached to a right arm, speed of the third midpoint, acceleration of the third midpoint, and deceleration of the third midpoint;
   at least one of a trajectory of a fourth midpoint of a straight line connecting a markers attached to left leg and a marker attached to a right leg, speed of the fourth midpoint, acceleration of the fourth midpoint, and deceleration of the fourth midpoint;
   at least one of a trajectory of a fifth midpoint of a straight line connecting a markers attached to the left arm and a marker attached to the right leg, speed of the fifth midpoint, acceleration of the fifth midpoint, and deceleration of the fifth midpoint;
   at least one of a trajectory of a sixth midpoint of a straight line connecting a markers attached to the left leg and a marker attached to the right arm, speed of the sixth midpoint, acceleration of the sixth midpoint, and deceleration of the sixth midpoint; and
   at least one of a trajectory of a gravity center of a plane or a solid including three markers attached to three out of the four limbs or four markers attached to the four limbs, speed of the gravity center, acceleration of the gravity center, and deceleration of the gravity center.

2. The infant movement analysis system according to claim 1, wherein said feature image extracting means is configured to extract a marker image of a reference point marker attached to at least one of head, breast, abdomen, and lumbar region other than the four limbs of the infant, and wherein said limit movement determining means is configured to determine the movement of each of the limbs based on an absolute position of the marker image of each of the limbs in the image and/or a relative position of the marker image of each of the limbs to a position of the marker image of the reference point marker in the image.

3. The infant movement analysis system according to claim 1, wherein said feature image extracting means is configured to extract marker images of markers attached to the four limbs of the infant that are coated with a phosphor or contain a substance that emits light when receiving ultraviolet.

4. An infant movement analysis system comprising:
   a database that stores movement data indicating histories of movements of four limbs of an infant, wherein the movements were determined from a motion picture of the infant photographed by an imaging device that photographed an infant and output a motion picture of the infant as digital data; and
   an analyzing device that is configured to determine movements of four limbs of the infant from the motion picture of the infant who is photographed by said imaging device and identifying a disease and/or a symptom of the infant from correlativity of movements of a plurality of arms and/or legs out of the four limbs
   wherein said analyzing device includes: a feature image extracting means for extracting once every one frame or plural frames, from an image of the infant, marker images of markers attached to the four limbs of the infant or feature images of the four limbs of the infant;
   a limb movement determining means for determining the movement of each of the limbs based on positions of the marker images or the feature images which are extracted in time series by said feature image extracting means;

a movement analyzing means for extracting from the movements of the four limbs determined by said limb movement determining means at least one of right-left synchronism of the arms or the legs, right-left symmetry of the arms or the legs, and coordination among the limbs; and a judging means for judging at least one of existence/nonexistence of a disease, a value of possibility of a disease and a symptom of the infant based on at least one of degree of the right-left synchronism, the right-left symmetry, and the coordination, which are extracted by said movement analyzing means wherein said movement analyzing means is configured to determine existence/nonexistence of the coordination among the limbs, or a degree of the coordination among the plural limbs, using as index one factor or a plurality of factors selected from:

a movement start order and movement start accelerations of the markers when the markers start moving from a stop state;

a movement stop order and movement stop decelerations of the markers when the markers stop from the moving state;

at least one of a trajectory of a first midpoint of a straight line connecting a marker attached to a right arm and a marker attached to a right leg, speed of the first midpoint, acceleration of the first midpoint, and deceleration of the first midpoint;

at least one of a trajectory of a second midpoint of a straight line connecting a marker attached to a left arm and a marker attached to a left leg, speed of the second midpoint, acceleration of the second midpoint, and deceleration of the second midpoint;

at least one of a trajectory of a third midpoint of a straight line connecting a markers attached to a left arm and a marker attached to a right arm, speed of the third midpoint, acceleration of the third midpoint, and deceleration of the third midpoint;

at least one of a trajectory of a fourth midpoint of a straight line connecting a markers attached to left leg and a marker attached to a right leg, speed of the fourth midpoint, acceleration of the fourth midpoint, and deceleration of the fourth midpoint;

at least one of a trajectory of a fifth midpoint of a straight line connecting a markers attached to the left arm and a marker attached to the right leg, speed of the fifth midpoint, acceleration of the fifth midpoint, and deceleration of the fifth midpoint;

at least one of a trajectory of a sixth midpoint of a straight line connecting a markers attached to the left leg and a marker attached to the right arm, speed of the sixth midpoint, acceleration of the sixth midpoint, and deceleration of the sixth midpoint; and at least one of a trajectory of a gravity center of a plane or a solid including three markers attached to three out of the four limbs or four markers attached to the four limbs, speed of the gravity center, acceleration of the gravity center, and deceleration of the gravity center.

5. The infant movement analysis system according to claim 4, wherein said feature image extracting means is configured to extract a marker image of a reference point marker attached to at least one of head, breast, abdomen, and lumbar region other than the four limbs of the infant, and wherein said limb movement determining means is configured to determine the movement of each of the limbs based on an absolute position of the marker image of each of the limbs and/or a relative position of the marker image of each of the limbs to a position of the marker image of the reference point marker in the image.

* * * * *

UNITED STATES PATENT AND TRADEMARK OFFICE
CERTIFICATE OF CORRECTION

PATENT NO.        : 7,591,793 B2
APPLICATION NO.   : 10/595593
DATED             : September 22, 2009
INVENTOR(S)       : Kensuke Orito et al.

It is certified that error appears in the above-identified patent and that said Letters Patent is hereby corrected as shown below:

Title Page item 73
The Assignee name set forth in the issued patent is incorrect. Please change the listed Assignee name of "Tokyo University of Agriculture and Technology" to the correct full name of --Tokyo University of Agriculture and Technology TLO Co., Ltd.--

Signed and Sealed this

Thirtieth Day of November, 2010

David J. Kappos
*Director of the United States Patent and Trademark Office*